United States Patent [19]
Katoh et al.

[11] Patent Number: 5,128,107
[45] Date of Patent: * Jul. 7, 1992

[54] APPARATUS FOR MAKING ESTER

[75] Inventors: Yoshihisa Katoh, Toyota; Takashi Ogawa; Mitsumasa Hasegawa, both of Kariya, all of Japan

[73] Assignee: Toshiba Ceramics Co., Ltd., Tokyo, Japan

[*] Notice: The portion of the term of this patent subsequent to Apr. 30, 2008 has been disclaimed.

[21] Appl. No.: 628,985

[22] Filed: Dec. 17, 1990

Related U.S. Application Data

[63] Continuation of Ser. No. 443,795, Nov. 24, 1989, abandoned, which is a continuation of Ser. No. 87,357, Aug. 20, 1987, abandoned.

Foreign Application Priority Data

Aug. 20, 1986 [JP] Japan .................. 61-194594

[51] Int. Cl.⁵ .................. B01J 10/00; B01D 35/16
[52] U.S. Cl. .................. 422/129; 422/131; 210/411; 210/497.01; 210/510.1
[58] Field of Search .................. 422/134, 135, 131, 129, 422/62; 210/435, 489, 490, 497.01, 500.1, 411, 510.1; 55/485, 522, 523; 202/202; 203/37, 47, DIG. 6

[56] References Cited

U.S. PATENT DOCUMENTS

| | | | |
|---|---|---|---|
| 2,855,100 | 10/1958 | Findlay | 210/412 |
| 3,002,963 | 10/1961 | Czenkusch et al. | 422/131 |
| 4,278,544 | 7/1981 | Takashima | 210/510.1 |
| 4,562,021 | 12/1985 | Alary et al. | 210/500.27 |
| 4,629,483 | 12/1986 | Stanton | 55/487 |
| 5,011,603 | 4/1991 | Katoh et al. | 210/497.1 |

Primary Examiner—Robert J. Warden
Assistant Examiner—William H. Beisner
Attorney, Agent, or Firm—Wegner, Cantor, Mueller & Player

[57] ABSTRACT

An apparatus for producing ester includes an esterification device, a neutralization device connected to the esterification device, a distillation device connected to the neutralization device, a container connected to the distillation device for storing ester distilled by the distillation device, a filter casing connected to the container, and a ceramic filter set in the filter casing for filtering the distilled ester in a cross flow manner.

3 Claims, 3 Drawing Sheets

APPARATUS FOR MAKING ESTER

This application is a continuation of U.S. application Ser. No. 07/443,795 filed Nov. 24, 1989, now abandoned, which is a continuation of U.S. application Ser. No. 07/087,357 filed Aug. 20, 1987, abandoned.

BACKGROUND OF THE INVENTION

This invention relates to an apparatus for producing ester.

An ester such as dibutylphthalate (DBP) or dioctylphthalate (DOP), which can be used as a plasticizer for polymers, is produced by a method including in order esterification, neutralization, distillation, decolorization and filtration. First, phthalic anhydride and alcohol such as butanol or octanol are heated so as to react whereby the monophthalate is produced. Next, to this reacted mixture is added sulfuric acid and benzene and then reacted at a boiling point so as to produce the diphthalate. This reacted mixture is neutralized by alkali and then distilled.

Since a Ti catalyst is used in producing the monophthlate, a by-product of Ti with an alkoxyl group is produced. Such a byproduct and Ti catalyst slightly remain in the distilled ester so that the ester is colored, thereby decreasing the quality. For such a reason, the distilled ester is decolorized with activated carbon for adsorbing the impurities. After that, the ester containing the activated carbon is filtered by a filter cloth coated with diatomaceous earth whereby the activated carbon can be removed from the ester so as to produce a final product.

The workability of the conventional ester production apparatus is not good because both the activated carbon and the filter msut be replaced and scrapped after. It also causes the production cost to increase.

If a nonuniform coating is formed on a filter cloth, the filtration accuracy is impaired so that final products can not have a high purity.

SUMMARY OF THE INVENTION

The object of this invention is to provide an apparatus for producing an ester in which the workability, production cost, purificaton and filtration accuracy can be improved.

DESCRIPTION OF THE EMBODIMENT

Figure 1:
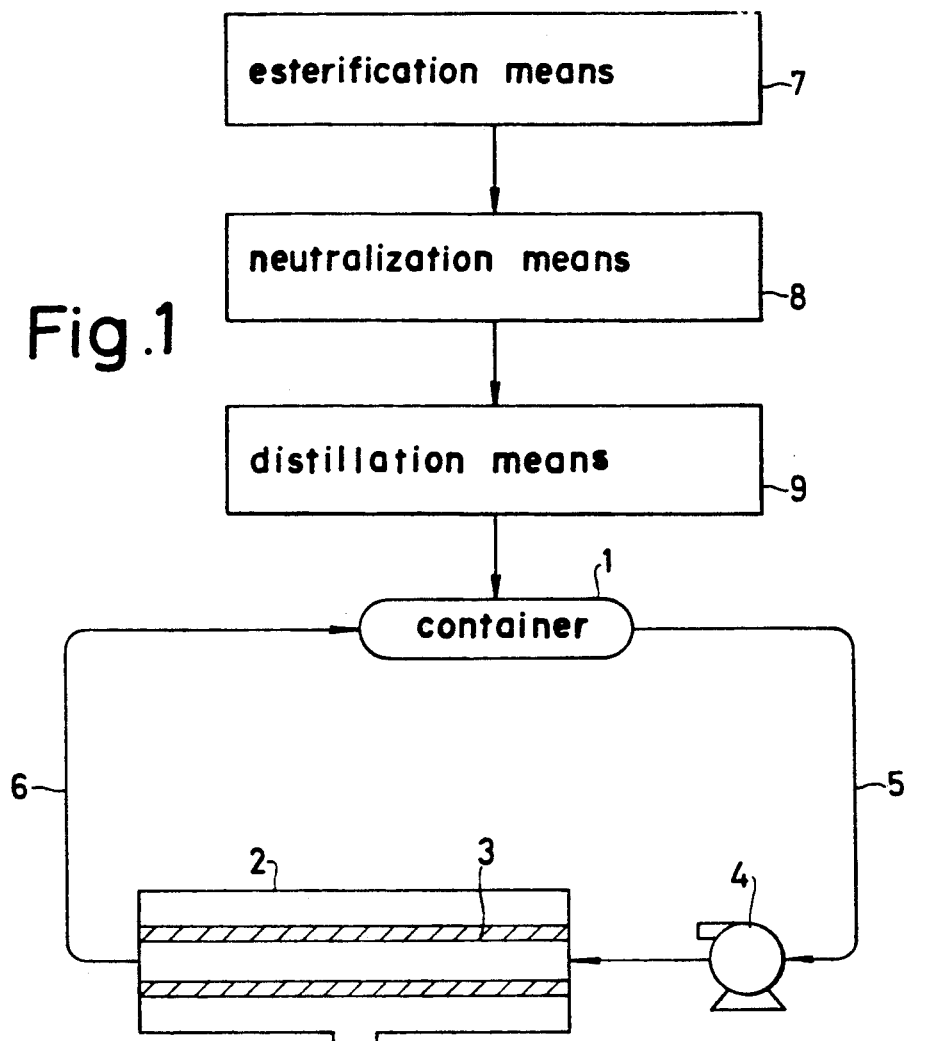
FIG. 1 is a schematic view showing an essential portion of an apparatus for producing an ester according to this invention.

Referring to FIG. 1, an apparatus for producing ester according to this invention includes a container 1 for storing ester after distilled, a filter casing 2 connected to the container 1 through circulating lines 5, 6, a ceramic filter 3 set in the filter casing 2, a pump 4 placed in the circulating line 5 between the container 1 and the filter casing 2, an esterification means 7, a neutralization means 8 connected to the esterification means 7 and a distillation means 9 connected to the neutralization means 8 and the container 1.

First, in the esterification means 7, phthalic anhydride and an alcohol such as butanol or octanol are heated so as to react, whereby the monophthalate is produced, and after that, to this reacted mixture is added sulfuric acid and benzene and then reacted at the boiling point or higher so as to produce the diphthalate. This reacted mixture is neutralized by alkali in the neutralization means 8 and then distilled in the distillation means 9, thereby to produce the distilled ester. This distilled ester is sent to the container 1. When the pump 4 feeds the distilled ester from the container 1 to the filter casing 2, the distilled ester is forced to pass through the ceramic filter 3 in such a way that a pressure in the filter 3 is larger than a pressure out of the ceramic filter 3. A cross-flow filtration is carried out. That is, the filtrate which has been filtered by the ceramic filter 3 is discharged through a port 2a of the filter casing 2 into a tank (not shown) for storing a final product. The distilled ester which has not been filtered by the filter 3 and still contains impurities such as Ti is sent back through the line 6 into the container 1.

Figure 2:
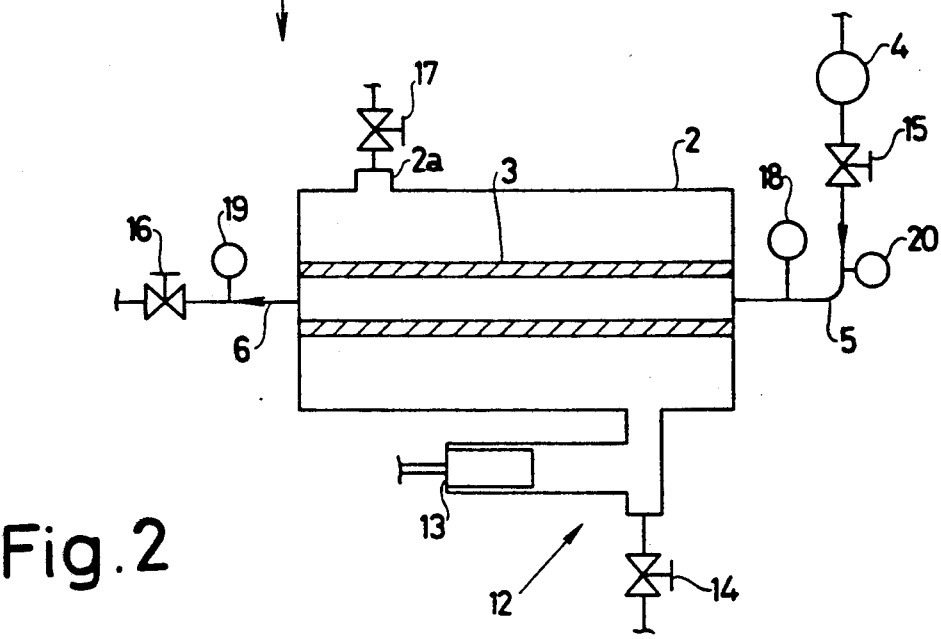
FIG. 2 is a schematic explanation view showing in detail a back wash device and its related portion of the apparatus of FIG. 1.

It is preferable that the ceramic filter 3 is backwashed in the filter casing 2. For example, as best shown in FIG. 2, a piston-cylinder type back washing device 12 is attached to the filter casing 2 so as to back wash the ceramic filter 3 by the filtrate remaining in the filter casing 2. A piston 13 can be actuated by an air cylinder means (not shown). Reference numerals 14 to 17 denote valves for controlling the liquid flow. Reference numerals 18 and 19 denote means for interrupting the liquid flow. The valves 14, 16 and 17 are closed when the ceramic filter 10 is back washed. Reference 20 denotes a flow meter.

The present application incorporates herein by reference U.S. Pat. No. 4,957,625, which discloses construction details of a filter unit using a ceramic filter such as that of the present invention, as well as a back wash system for cleaning the filter during use, and U.S. Pat. No. 5,011,603, which is directed to the ceramic filter used in this invention. The present application further incorporates by reference U.S. Pat. No. 4,839,488, which discloses a different specific use for the filter used in this invention, i.e., for filtering dielectric fluid in electric discharge engraving.

Preferably, the ceramic filter 3 includes a filter layer having a thickness of 10 to 40 micron meters (hereinafter called merely microns) from a filter surface. When it is measured by a mercury porous-meter, a cumulative intrusion volume of all pores in the filter layer is 0.2 cc/g or less. A cumulative intrusion volume of the pores having pore diameters of 0.1 to 3.0 microns is 0.1 cc/g or more. A cumulative intrusion volume (H) of the pores ranging within the pore diameter width (w) of 0.1 microns around a center pore diameter (PD) which is a pore diameter in case of a half of a cumulative intrusion volume (IV) at a pore diameter of 0.1 microns is 50% or more of a cumulative intrusion volume of all pores.

If the thickness of the filter layer is less than 10 microns, high strength can not be obtained, and nonuniformity can not be avoided. If it is more than 40 microns, the filtration performance is decreased, and the filter layer is sometimes broken away due to heat expansion.

If the cumulative intrusion volume of all pores is more than 0.2 cc/g, a desired strength can not be easily obtained. If the cumulative intrusion volume of the pores having a pore diameter of 0.1 to 3.0 microns is less than 0.1 cc/g, the filtration rate is decreased.

Figure 3:
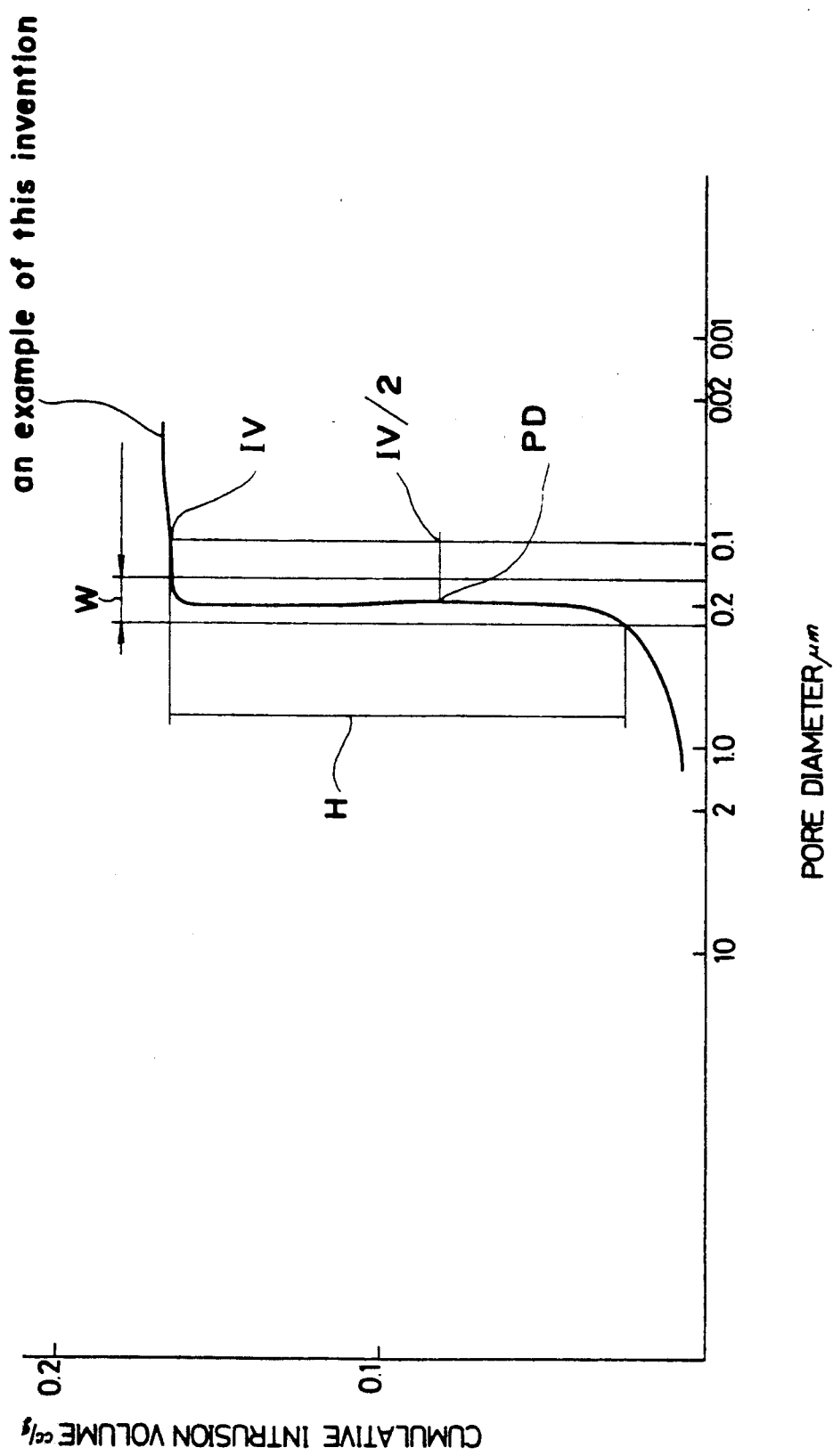
FIG. 3 is a graph showing the relationship between pore diameter and cumulative intrusion volume of a ceramic filter for use in the apparatus of FIGS. 1 and 2.

Referring to FIG. 3 showing an example of the ceramic filter, the cumulative intrusion volume of all pores is 0.18 cc/g.

The cumulative intrusion volume of the pores having a pore diameter of 0.1 to 3.0 microns is 0.17 cc/g. The center pore diameter (PD) is 0.2 microns. The cumulative intrusion volume (H) of the pores ranging within a pore diameter width (W) of 0.1 microns is 0.12 cc/g, the percentage of which is 66.7%. This cumulative intrusion volume (H) is larger than a half of the cumulative intrusion volume (IV) at a pore diameter of 0.1 microns.

The filter layer preferably includes plural layers, for example, such as an intermediate layer coated on the inner surface of a support layer and an inner layer coated on the intermediate layer. The intermediate layer may be made of alumina powders having a particle size of 2 to 10 microns, and the inner layer may be made of alumina powders having a particle size of 0.4 to 1 microns.

In the embodiment of FIG. 2, the ceramic filter 3 is formed in the shape of a pipe having an inner diameter of 15 mm and an outer diameter of 19 mm. The filter layer has pore diameters of 1.5 microns and 10 microns.

Figure 4:
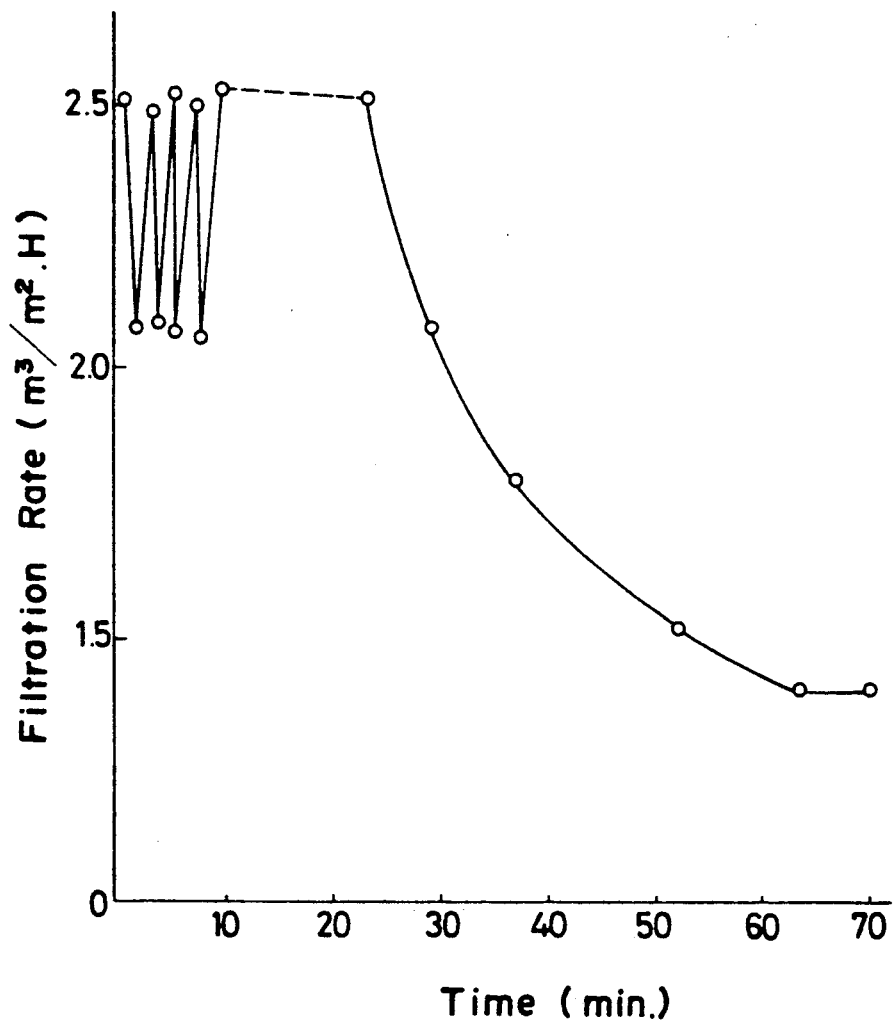
FIG. 4 is a graph showing the relationship between time and filtration rate of a filter device for use in the ester production apparatus of FIGS. 1 and 2.

FIG. 4 shows the relationship between time and filtration rate of the ceramic filter 3 when the dioctylphthalate is filtered in the ester production apparatus of FIGS. 1 and 2. After the dioctylphthalate is distilled, it is filtered at a circulating speed of 3 m/sec with a pressure difference of 0.5 Kg. As shwon in FIG. 4, the back washing is repeated only within 20 minutes after the filtration starts.

As can be seen from FIG. 4, a good filtration rate can be obtained if the back washing is repeated. Thus, a filter can have a long life time so that the replacement of filters is not often required whereby the workability and cost reduction can be improved.

Table 1 shows the filtration accuracies in terms of concentration of Ti and the like. The starting liquid is the dioctylphthalate which is distilled and not filtered. The comparative example is the diocytylphthalate which is distilled and then filtered by a conventional filter cloth coated with diatomaceous earth. The example 1 is the dioctylphthalate which is distilled and then filtered by a ceramic filter having a pore diameter of 0.5 microns which is set in the apparatus of FIGS. 1 and 2. The example 2 is the dioctylphalate which is distilled and then filtered by a ceramic filter having a pore diameter of 10 microns. The examples 1 and 2 are within the scope of this invention. The comparative example is out of the scope of this invention.

As can be seen from Table 1, even if no active carbon is used, the impurities such as Ti and Ti having alkoxyl group can be filtered so as to be removed from the distilled ester. Thus, a high quality of ester which is not colored can be produced.

TABLE 1

|  | Ti (ppm) | $\begin{array}{c} RO\diagdown\diagup OR \\ Ti \\ RO\diagup\diagdown OR \end{array}$ (mg/kg) |
|---|---|---|
| Starting Liquid | 1.6 | 9.5 |
| Comparative Example | 1.1 | 4.9 |
| Example 1 | less than 0.3 | less than 1.8 |
| Example 2 | less than 0.3 | less than 1.8 |

We claim:

1. An apparatus for producing an ester, comprising an esterification means, a neutralization means connected to the esterification means, a distillation means connected to the neutralization means, a container in flow communication with the distillation means for storing ester distilled by the distillation means, a filter casing connected to the container, the filter casing having a port through which filtrate can be sent through the port to a tank, and a ceramic filter set in the filter casing for filtering the distilled ester in a cross flow manner, the ceramic filter being formed in the shape of a pipe and comprising a ceramic support layer having an inner surface and a ceramic filter layer coated on the inner surface of the support layer, the filter layer having a thickness of 10 to 40 microns, a back washing device attached to the filter casing for back washing the ceramic filter with the filtrate remaining in the filter casing, the back washing device comprising a cylinder means and a piston movably set in the cylinder means, the filter layer having a cumulative intrusion volume of pores having pore diameters of 0.1 to 3.0 microns which is 0.1 cc/g or more and a cumulative intrusion volume (H) of the pores ranging within a pore diameter width (W) 0.1 microns around a center pore diameter (PD) which is 50% or more of a cumulative intrusion volume of all pores in the filter layer, the filter layer including an intermediate layer coated on the inner surface of the support layer and an inner layer coated on the intermediate layer.

2. The apparatus of claim 1, wherein the filter layer is made of an alumina ceramic material having a high purity.

3. The apparatus of claim 1, wherein the intermediate layer is made of alumina powders having a particle size of 2 to 10 microns, and the inner layer is made of alumina powders having a particle size of 0.4 to 1 microns.

* * * * *